United States Patent
Wang et al.

(10) Patent No.: US 10,405,543 B2
(45) Date of Patent: Sep. 10, 2019

(54) MICROCAPSULE COMPOSITIONS AND THE METHOD OF THEIR RELEASE

(71) Applicants: Rohm and Haas Company, Collegeville, PA (US); The Board of Trustees of the University of Illinois, Urbana, IL (US)

(72) Inventors: Hsuan-Chin Wang, Urbana, IL (US); Steven C. Zimmerman, Champaign, IL (US); David M. Laganella, Swedesboro, NJ (US)

(73) Assignees: Rohm and Haas Company, Collegeville, PA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/729,998

(22) Filed: Oct. 11, 2017

(65) Prior Publication Data

US 2018/0116212 A1     May 3, 2018

Related U.S. Application Data

(60) Provisional application No. 62/414,962, filed on Oct. 31, 2016.

(51) Int. Cl.
*A01N 25/28*     (2006.01)
*A01N 33/04*     (2006.01)
*A01N 43/80*     (2006.01)
*A01N 43/68*     (2006.01)
*A01N 37/10*     (2006.01)

(52) U.S. Cl.
CPC ............. *A01N 25/28* (2013.01); *A01N 33/04* (2013.01); *A01N 37/10* (2013.01); *A01N 43/68* (2013.01); *A01N 43/80* (2013.01); *A01N 2300/00* (2013.01)

(58) Field of Classification Search
None
See application file for complete search history.

(56) References Cited

U.S. PATENT DOCUMENTS 6,022,501 A   *   2/2000   Dexter .................. A01N 25/28
                                                                                264/4.7
7,790,225 B1     9/2010   Calle et al.

FOREIGN PATENT DOCUMENTS

CN            101735163 B   *   10/2012

OTHER PUBLICATIONS

SciFinder abstract for CN 101735163, original document published Oct. 2012 (Year: 2012).*

* cited by examiner

*Primary Examiner* — Nissa M Westerberg
(74) *Attorney, Agent, or Firm* — Tifani M. Edwards

(57) ABSTRACT

The present invention provides microcapsules with good barrier properties and the ability to release encapsulated hydrophobic liquids at low and high pH.

6 Claims, No Drawings

MICROCAPSULE COMPOSITIONS AND THE METHOD OF THEIR RELEASE

This invention relates to microcapsule compositions which have the ability to provide for a pH triggered release of hydrophobic liquids.

High capacity, thin-shell microcapsules with good barrier properties and the ability to release encapsulated actives at the desired rates upon application of suitable triggers are in high demand in industrial settings. Attempts to make pH triggered encapsulates exist in the art. U.S. Pat. No. 6,022,501 describes using excess acid halides to generate carboxylic acid groups in microcapsule shells. Although U.S. Pat. No. 6,022,501 describes a triggered release system, such a system utilizes pH greater than 5.9 as the trigger. Additionally, in the prior art relatively few compositions describe an alkaline/high pH triggered release. Rarer still is the use of both high and low pH to trigger degradation/release in a single system; most of these are polyampholyte-based encapsulants.

What is needed in the art is the ability for the same microcapsule chemistry to be utilized in triggered-release applications under different pH environments without the need for different encapsulation/triggered release strategies. The present invention solves the deficiencies of the art.

The present invention provides a microcapsule composition comprising a core comprising a hydrophobic liquid; and a shell comprising the reaction product of at least one simple diester diacid chloride monomer and at least one polyamine.

The present invention also provides a method of releasing a hydrophobic liquid wherein the method comprises placing a microcapsule composition comprising a core comprising a hydrophobic liquid; and a shell comprising the reaction product of at least one simple diester diacid chloride monomer and at least one polyamine into an aqueous environment having a pH of 9 or greater.

The present invention also provides a method of releasing a hydrophobic liquid wherein the method comprises placing a microcapsule composition comprising a core comprising a hydrophobic liquid; and a shell comprising the reaction product of at least one simple diester diacid chloride monomer and at least one polyamine into an aqueous environment having a pH of 6 or less.

As used herein by "hydrophobic liquid" is meant a water insoluble compound that is a liquid at the reaction temperature or a water insoluble compound dissolved in a hydrophobic solvent that is liquid at the reaction temperature.

As used herein by "hydrophobic solvent" is meant a liquid that has a solubility in water of less than 5%.

As used herein by "high pH" is meant pH of 8 or greater, preferably pH 9 to 12, more preferably pH 10 to 11.

As used herein by "low pH" is meant pH of 6 or lower, preferably pH 4 to 6 more preferably pH 4 to 5.

As used herein by "neutral pH" is meant pH of greater than 6 to less than 8, preferably 7-8.

As used herein "microcapsules" and "microencapsulated compositions" are used interchangeably.

As used herein by "reaction temperature" is the temperature at which the simple diester diacid chloride monomer and the polyamine are reacted to form the shell. Suitable temperatures include 0-99° C., alternatively 15-60° C., further alternatively 20-50° C., and further alternatively 40-50° C.

As used herein by "water insoluble" is meant a solubility of less than 5% and more particularly less than 2% in water at room temperature.

Microcapsule compositions of the present invention comprise a core and a shell wherein the shell comprises the reaction product of at least one simple diester diacid chloride monomer and at least one polyamine. A particularly useful diester diacid chloride monomer of the present invention is pyromellitic diester diacid chloride (PDDC) and particularly useful polyamines of the present invention are N,N',N"-tris (2-aminoethyl)-1,3,5-triazine-2,4,6-triamine (triazine) and diethylenetriamine (DETA). The core of the microcapsule compositions is comprised of a hydrophobic liquid.

The microcapsule compositions of the present invention encapsulate in its core hydrophobic liquids. Examples of suitable hydrophobic liquids in this encapsulated liquid core include but are not limited to 4,5-dichloro-2-n-octyl-3(2H)-isothiazolone (DCOIT), 2-n-octyl-3(2H)-isothiazolone (OIT) and benzisothiazolone (BIT), lodopropargyl butyl carbamate (IPBC), Propiconazole, N(trichloromethylthio) pthalimide, methyl benzimidazol-2-yl carbamate, tetrachloroisophthalonitrile, Dibromonitriloprorianamide (DBNPA), 2-(thiocyanomethylthio)benzothiazole (TCMTB), Tebuconazole, Tributyl tin benzoate, Parabens, 2,5-dimethyl-N-cyclohexyl-N-methoxy-3-furan carboxamide, 5-Ethoxy-3-trichloromethyl-1,2,4 thiadiazole, 3-(2-methyl piperidino) propyl 3,4-dichlorobenzoate, N,N'-(1,4-piperazinediyl bis (2,2,2-trichloro)ethylidene) bis formamide, Tetramethyl thiuram disulfide, 0-Ethyl-S,S,diphenyl-dithiophosphate, 5,10-dihydro-5,10-dioxo naphtho (2,3,9)-p-dithiin-2,3-dicarbonitrile, .alpha.-2-[(4-chlorophenyl)ethyl]-.alpha.-(1,1-dimethyl ethyl)-1H-1,2,4-triazole-1-ethanol 3-(3,4-dichlorophenyl)1,1 dimethylurea, N-tridecyl-2,6-dimethylmorpholine and 4-N-dodecyl-2,6-dimethylmorpholine or solutions thereof. A particularly preferred hydrophobic liquid is—dichloro-2-n-octyl-3(2H)-isothiazolone (DCOIT). The hydrophobic liquid may be present in the core alone or in combination with a hydrophobic solvent either as a mixture or as a dispersion. The encapsulated liquid core comprises up to 95% of the total microcapsule capsule weight. Advantageously, the hydrophobic liquid does not release from the core when the microcapsules of the present invention are suspended in hydrophobic solvent. Such hydrophobic solvent may be, for example, toluene, xylenes, ethyl acetate, hexanes, heptanes, benzene, naphthalene, 2-butanone, or mixtures thereof.

The resultant microcapsule compositions of the present invention have capsule diameters between 200 and 350 μm, with shell thicknesses in the range of 0.8-1.5 μm. Capsules outside of this size range are easily envisioned by one skilled in the art. Detailed characterization of capsule morphology, size, and shell-thickness was performed by scanning electron microscopy (SEM). The shell-thickness was determined by cutting capsules with a razor blade and imaging the cross-section. These compositions exhibit resistance to leakage in dry or non-polar environments, and demonstrate pH tunable release of hydrophobic liquids at high and low pH. Particularly interesting is the microcapsule composition's ability to undergo accelerated release of a small molecule active at high and low pH's, while at neutral/physiological pH, sustain a steady release profile. Such capability allows the same microcapsule chemistry to be utilized in triggered-release applications under different pH environments without the need for different encapsulation/triggered release strategies.

The hydrophobic liquids described herein may be released from the microcapsules by placing them either in high or low pH aqueous environments. Any aqueous environment which has either a high or low pH is suitable. Non-limiting pH ranges suitable for the present invention include pH 9 or greater and 6 or lower; however, all ranges in the definition of high and low pH are contemplated.

EXAMPLES

Method of Making:

The microcapsules of the present invention were prepared by interfacial polymerization based on a slight modification of procedure reported by Frechet in Broaders, K. E.; Pastine, S. J.; Grandhe, S.; Fréchet, J. M. J. *Chemical Communications* 2011, 47, 665. A saturated solution of pyromellitic diester diacid chloride (PDDC) in toluene was emulsified with an aqueous 0.4 w/w % polyvinyl alcohol solution with magnetic stirring to produce a suspension of oil-in-water emulsion droplets, whose shapes and sizes determine the final capsule dimensions. Dropwise addition of an aqueous solution of the hydrophilic monomers, triazine and DETA initiated the polycondensation reactions at the water-oil interface to form a cross-linked polyamide shell. Maturation for 60 min afforded a suspension of microcapsules that were vacuum filtered, rinsed with DI water and acetone, and allowed to dry in air to give a white, free flowing powder.

The percent of hydrophobic liquid dye solution, comprising a dye mixed with toluene, released at various points in time at low, neutral, and high pH is captured in the tables below.

TABLE 1

| 1:1 Triazine:DETA - terephthaloyl chloride (TC) (Control) | | | | |
| --- | --- | --- | --- | --- |
| Time (h) | pH 5 | pH 7 | pH 10 | Toluene |
| 2 | −2.65 | −3.06 | −2.74 | −4.86 |
| 12 | 0.70 | −1.45 | −0.18 | −4.30 |
| 24 | 3.66 | −0.16 | 2.23 | −3.56 |
| 50 | 5.92 | 0.64 | 3.82 | −4.12 |
| 72 | 5.33 | 0.32 | 4.63 | −5.81 |
| 96 | 6.06 | −0.16 | 5.91 | −5.80 |
| 120 | 9.45 | 2.25 | 9.44 | −4.12 |

TABLE 2

| 3:1 Triazine:DETA - PDDC | | | | |
| --- | --- | --- | --- | --- |
| Time (h) | pH 5 | pH 7 | pH 10 | Toluene |
| 3 | 2.80 | 0.27 | 1.88 | −2.42 |
| 13 | 10.79 | 3.84 | 8.99 | −1.83 |
| 24 | 21.44 | 6.92 | 22.85 | −2.56 |
| 48 | 39.71 | 14.04 | 60.19 | −2.79 |
| 72 | 54.58 | 22.35 | 86.51 | −2.08 |
| 96 | 64.97 | 31.50 | 96.82 | −2.29 |
| 120 | 72.11 | 41.60 | 100.35 | −1.39 |

TABLE 3

| 1:1 Triazine:DETA - PDDC | | | | |
| --- | --- | --- | --- | --- |
| Time (h) | pH 5 | pH 7 | pH 10 | Toluene |
| 3 | 4.76 | −3.96 | 3.66 | −3.29 |
| 13 | 26.66 | 1.19 | 30.58 | −3.69 |
| 24 | 51.46 | 9.79 | 69.54 | −3.83 |
| 48 | 83.89 | 35.71 | 97.54 | −4.24 |
| 72 | 98.41 | 66.52 | 101.38 | −3.27 |
| 96 | 101.61 | 90.05 | 100.67 | −3.42 |
| 120 | 104.43 | 103.27 | 102.45 | −3.41 |

We claim:

1. A microcapsule composition comprising:
   i) a core comprising a hydrophobic liquid; and
   ii) a shell comprising the reaction product of at least one simple diester diacid chloride monomer and N,N',N"-tris-(2-aminoethyl)-1,3,5-triazine-2,4,6-triamine.

2. The microcapsule composition of claim 1 wherein the simple diester diacid chloride monomer is pyromellitic diester diacid chloride.

3. The microcapsule composition of claim 1 wherein the hydrophobic liquid is 4,5-dichloro-2-n-octyl-3(2H)-isothiazolone.

4. The microcapsule composition of claim 1 wherein the hydrophobic liquid is a solution of dichloro-2-n-octyl-3(2H)-isothiazolone in a hydrophobic solvent.

5. A method of releasing a hydrophobic liquid wherein the method comprises placing a microcapsule composition comprising:
   i) a core comprising a hydrophobic liquid; and
   ii) a shell comprising the reaction product of at least one simple diester diacid chloride monomer and N,N',N"-tris-(2-aminoethyl)-1,3,5-triazine-2,4,6-triamine
   into an aqueous environment having a pH of 6 or less.

6. A method of releasing a hydrophobic liquid wherein the method comprises placing a microcapsule composition comprising:
   iii) a core comprising a hydrophobic liquid; and
   iv) a shell comprising the reaction product of at least one simple diester diacid chloride monomer and N,N',N"-tris-(2-aminoethyl)-1,3,5-triazine-2,4,6-triamine
   into an aqueous environment having a pH of 9 or greater.

* * * * *